(12) United States Patent
Weigel (10) Patent No.: US 11,129,324 B2
(45) Date of Patent: Sep. 28, 2021

(54) SENSOR DEVICE FOR DETERMINING THE POSITION OF SEEDS WHILE SOWING, SOWING SYSTEM AND METHOD FOR DETERMINING THE POSITION OF SEEDS IN A TRENCH

(71) Applicant: BAUMER ELECTRIC AG, Frauenfeld (CH)

(72) Inventor: Michael Weigel, Muellheim (CH)

(73) Assignee: BAUMER ELECTRIC AG, Frauenfeld (CH)

( * ) Notice: Subject to any disclaimer, the term of this patent is extended or adjusted under 35 U.S.C. 154(b) by 415 days.

(21) Appl. No.: 16/044,595

(22) Filed: Jul. 25, 2018

(65) Prior Publication Data
US 2019/0029167 A1    Jan. 31, 2019

(30) Foreign Application Priority Data
Jul. 27, 2017 (EP) .................................... 17183613

(51) Int. Cl.
*A01C 7/10*    (2006.01)
*A01C 21/00*   (2006.01)
(Continued)

(52) U.S. Cl.
CPC ............... *A01C 7/105* (2013.01); *A01C 1/00* (2013.01); *A01C 7/12* (2013.01); *A01C 21/005* (2013.01);
(Continued)

(58) Field of Classification Search
CPC .. A01C 7/105; A01C 7/12; A01C 1/00; A01C 21/005; G01J 1/08; G01J 1/42; G01J 1/58
See application file for complete search history.

(56) References Cited

U.S. PATENT DOCUMENTS 6,080,950 A * 6/2000 Jalink ..................... A01C 1/025
                                                                209/576
6,373,057 B1   4/2002 Penfold
(Continued)

FOREIGN PATENT DOCUMENTS

DE   10 2004 011 302 A1   9/2005
EP      0 988 779 A1      3/2000
(Continued)

*Primary Examiner* — Alicia Torres
(74) *Attorney, Agent, or Firm* — Norman B. Thot (57) ABSTRACT

A sensor device for determining a position of seeds while sowing. The sensor device includes a radiation assembly which generates an illumination radiation oriented towards a target area, and a detection assembly. The radiation assembly includes a radiation source which provides an emission spectrum of the illumination radiation covering a spectral range. The detection assembly includes a radiation detector which detects an incident radiation, and a filter member with an attenuation band and a pass band. The radiation detector includes a field of view. The pass band has an attenuation which is less than an attenuation of the attenuation band in a wavelength range where the wavelengths are longer than those of the attenuation band. The target area and the field of view intersect. The radiation source and the radiation detector form a triangulation arrangement so that a distance from the target area to the detection assembly can be determined.

15 Claims, 3 Drawing Sheets

(51) Int. Cl.
  *G01J 1/08* (2006.01)
  *G01J 1/58* (2006.01)
  *G01J 1/42* (2006.01)
  *A01C 1/00* (2006.01)
  *A01C 7/12* (2006.01)
  *G01N 33/52* (2006.01)

(52) U.S. Cl.
  CPC . *G01J 1/08* (2013.01); *G01J 1/42* (2013.01); *G01J 1/58* (2013.01); *G01N 33/52* (2013.01)

(56) References Cited

U.S. PATENT DOCUMENTS

| | | | |
|---|---|---|---|
| 2003/0130054 A1* | 7/2003 | Bissonnette | A63B 43/008 473/199 |
| 2011/0143936 A1* | 6/2011 | Hunter | G01N 21/85 504/100 |
| 2012/0042813 A1 | 2/2012 | Liu et al. | |
| 2012/0279314 A1* | 11/2012 | Hien | G01N 22/00 73/861 |
| 2013/0021469 A1* | 1/2013 | Conrad | G06K 9/00 348/135 |

FOREIGN PATENT DOCUMENTS

| | | |
|---|---|---|
| EP | 2 420 120 A1 | 2/2012 |
| WO | WO 99/56127 A1 | 11/1999 |

\* cited by examiner

SENSOR DEVICE FOR DETERMINING THE POSITION OF SEEDS WHILE SOWING, SOWING SYSTEM AND METHOD FOR DETERMINING THE POSITION OF SEEDS IN A TRENCH

CROSS REFERENCE TO PRIOR APPLICATIONS

Priority is claimed to European Patent Application No. EP 17183613.3, filed Jul. 27, 2017. The entire disclosure of said application is incorporated by reference herein.

FIELD

The present invention relates to a sensor device for determining the position of seeds, for example, the counting of seeds, while sowing, in particular for a sowing system, wherein the sensor device comprises a radiation assembly for generating illumination radiation oriented towards a target area, the radiation assembly having an emission spectrum covering at least a first spectral range, and a detection assembly with at least one radiation detector for detecting incident radiation, the at least one detector having at least one field of view, wherein the at least one target area and the at least one field of view intersect, and wherein the detection assembly is provided with at least one filter member, the at least one filter member having an attenuation band and a pass band, the pass band having less attenuation than the attenuation band in a wavelength range whose wavelengths are longer than those of the attenuation band. The present invention further relates to a sowing system for delivering seeds into soil, and to a method for determining the position of seeds in a trench.

BACKGROUND

In agriculture, the position of seeds in soil, in particular the depth of seeds in soil, has a significant impact on the emergence of the plants and on yield. Another factor having a significant impact on yield is the spacing between two adjacent seeds in the soil. This spacing may also be seen as a part of the seed position. In common sowing systems, a trench is opened in soil, seeds are placed in the trench, and the trench is then closed. For determining the depth of the seeds in the soil, the seeds are again uncovered and the depth is measured manually. This is time-consuming and has the further drawback that the position is only determined subsequent to placing the seeds in the soil.

EP 0 988 779 A1 describes a device for counting and detecting seeds inside a chute. The device comprises an emitter and a detector for detecting seeds in a predefined range. A monitoring system for a sowing system which is capable of detecting seeds is described in DE 10 2004 011 302 A1. A system for measuring seed distance during sowing is described in EP 2 420 120 A1.

SUMMARY

An aspect of the present invention is to provide a sensor device, a sowing system, and a method as mentioned above which allow the seed position to be determined during sowing in order to facilitate a controlled sowing and thereby improving yield.

In an embodiment, the present invention provides a sensor device for determining a position of seeds while sowing. The sensor device includes a radiation assembly configured to generate an illumination radiation which is oriented towards at least one target area, and at least one detection assembly. The radiation assembly comprises at least one radiation source which is configured to provide a first emission spectrum of the illumination radiation which covers at least a first spectral range. The at least one detection assembly comprises at least one radiation detector configured to detect an incident radiation, and at least one filter member comprising an attenuation band and a pass band. The at least one radiation detector comprises at least one field of view. The pass band comprises an attenuation which is less than an attenuation of the attenuation band in a wavelength range where the wavelengths are longer than those of the attenuation band. The at least one target area and the at least one field of view intersect. The at least one radiation source of the radiation assembly and the at least one radiation detector form a triangulation arrangement which is configured so that a distance from the at least one target area to the at least one detection assembly can be determined.

BRIEF DESCRIPTION OF THE DRAWINGS

The present invention is described in greater detail below on the basis of embodiments and of the drawings in which.

DETAILED DESCRIPTION

The sensor device allows the position of seeds during sowing to be determined. A direct reaction on the sowing process is therefore possible if the seeds are not placed in the optimal position. In particular in the case where seeds are provided with at least one seed marker, the at least one filter member may facilitate the detection of radiation emitted by the seeds by blocking the illumination radiation provided by the radiation assembly and/or ambient radiation. This detection of the seeds, which is a form of optical identification, may be used to observe the presence of seeds and/or to measure the distance of the seeds to the device in order to determine the depth of the seeds in the trench. Since a sowing system is usually moved along the trench during sowing, the detection of two adjacent seeds during movement of the sowing system or at least of the sensor device may also be used to calculate the distance between these two adjacent seeds. The depths of the seeds in the soil may be determined either by the radiation emitted by the seeds or by the surrounding soil. The depth of the trench can in this case be measured so that the depth of the seeds in that trench is indirectly derived.

The target area may in particular be chosen in such a position where the seed is still in flight, and/or the seed can be detected both in flight and on the ground. The advantage thereby is that an occlusion by the soil does not affect the ability to detect the seed. The final position can be estimated by extrapolating the final resting position by known seed speed, vehicle speed, and distance to the trench ground.

For the sowing system as mentioned above, the sowing system comprises at least one sensor device according to the present invention, a cutting device for cutting a trench, a placement device for placing seeds in the trench, and a closing device for closing the trench. The sowing system according to the present invention may also benefit from the aforementioned advantages of the sensor system according to the present invention.

For the method as mentioned above, the method comprises the steps of irradiating at least one target area with illumination radiation, detecting incident radiation received from the target area having longer wavelengths than the illumination radiation with at least one detector assembly, determining the distance of the target area to the detection assembly in dependence from a position where the incident radiation is received, and determining the presence of a seed by optical identification.

The present invention can be further improved via various individually advantageous configurations which can be combined with one another as desired. These configurations and the associated advantages are explored in greater detail below. The features of the sensor device and the sowing system according to the present invention described below may thereby be used for the method according to the present invention and vice versa.

In order to facilitate the determination of the distance between the target area or an object therein and the sensor device, the radiation assembly may comprise at least one radiation source that is spaced apart from the at least one detector, wherein a triangle is formed between the at least one radiation source, the at least one detector, and a region in which the at least one target area and the at least one field of view intersect. In other words, the at least one radiation source and the at least one detector form a triangulation arrangement adapted for determining a distance from the target area to the at least one detector assembly. Triangulation is a reliable way for determining distances.

The at least one radiation source may be adapted for irradiating a spot-like area at least in the field of view of the at least one detector, and the at least one detector may be provided with at least one one-dimensional sensor array. A simple triangulation arrangement can thereby be formed. Radiation that is emitted by a seed in the trench, for example, a reflection of the illumination radiation or an emission induced by the illumination radiation, may enter the at least one detector at a certain position of the one-dimensional sensor array. The distance to the seed may be calculated depending on the position of the incident radiation on the one-dimensional sensor array because the distance between the radiation assembly and the detector assembly is known. In order to further calculate the relative position of a seed in the trench with respect to the ground, the distance between the sensor device and the ground can be used. The distance between the seed and the ground and the distance between the ground and the sensor device consequently sum up to the distance between the seed and the sensor device. The one-dimensional sensor array may in particular be formed by a CMOS line sensor. A longitudinal direction of the one-dimensional sensor array can, for example, be parallel with the aforementioned triangle between the radiation source, the detector assembly, and the target area. The one-dimensional sensor array can further, for example, be arranged basically perpendicular to a direct line between the at least one detector and the region in which the at least one target area and the at least one field of view intersect. If no seeds are present in the field of view, this setup may also be used to only determine the depth of the trench. Emission of radiation from the soil that is induced by the illumination radiation may in this case be detected by the detection assembly.

In order to detect not only the presence of seeds and/or depth of seeds in the soil, the at least one radiation source may be adapted for irradiating a line-like area at least in the field of view of the at least one detector, wherein the at least one detector is provided with at least one two-dimensional sensor array. Radiation that is reflected not only by seeds, but also by the trench or, if no seeds are in the field of view, only by the trench can in this case be detected by the two-dimensional sensor array so that a trench profile can be determined. In other words, a line may be projected with the illumination radiation in the target area and a trench profile may be determined by a space-resolved evaluation of the incident radiation. The line-like area of illumination radiation should in this case basically be arranged perpendicular to a longitudinal direction of the trench. The two-dimensional sensor array can, for example, be formed by a CMOS array. The two-dimensional sensor array can, for example, also be arranged basically perpendicular to a direct line between the at least one detector and the region in which the at least one target area and the at least one field of view intersect. Finally, the at least one radiation source and the at least one radiation detector can, for example, be arranged so that a plane formed by the aforementioned triangle is parallel with the longitudinal direction of the trench.

The wavelengths of the first spectral range is matched with the fluorescent substance (seed marker), which is usually less than 450 nm, for example, less than 300 nm. A fluorescence arrangement can thereby be formed. This illumination radiation may be used to induce fluorescence in either the soil or in the seeds or in both. Inducing emission of the seeds may be facilitated by using seeds that are provided with fluorescent markers as seed markers. The at least one filter member can, for example, be adapted for letting only the induced radiation of the seeds pass to the at least one radiation detector. Such induced emitted radiation is generally in the visible range.

In order to further improve the determination of the seed position, the detector assembly may further comprise at least one further filter member and at least one further radiation detector, wherein the at least one further filter member is adapted to let radiation of the first spectral range pass. In this setup, the further filter member and the further detector may be used to perform the triangulation, wherein this radiation detector and this filter member are adapted for detecting the illumination radiation. The other radiation detector and other filter member of the system or, in other words, the first radiation detector and the first filter member, may be used for seed detection by detecting only radiation that passes the pass band. If a fluorescence arrangement is used, the seed detection can be performed using fluorescence and the depth measurement and/or trench profiling can be performed by directly using the illumination radiation for the triangulation.

The sensor device may further be improved by the radiation assembly being further provided with at least one further radiation source for providing at least one second spectral range, wherein the wavelengths of the second spectral range are longer than those of the first spectral range. The detection of seeds and the depth measurement, either of a seed in the trench or of the trench only, can here be separated. A fluorescence arrangement may be used to detect seeds in the trench. For determining the depth of the trench and/or the trench profile, radiation can be used that has a different spectral range then the illumination radiation, for example, in the visible spectrum.

The sowing system according to the present invention can be further improved by the sowing system further comprising at least one marking device for marking seeds prior to placing the seeds in the trench. The seeds can be provided with seed markers that may facilitate the detection of seeds in the trench and/or the depth measurement when using the sensor device. The marking device can, for example, in particular be adapted for marking the seeds with at least one fluorescent substance. The fluorescent substance can, for example, be a non-toxic substance that does not harm the seeds. The fluorescent substance can, for example, be riboflavin (E101), certain marine algae, or curcumin (E100).

The marking device may be adapted for spraying or brushing the at least one seed marker onto the seeds. The marking device may also be adapted to use other appropriate ways for providing the seeds with seed markers. The marking device can, for example, provide a bath for the seeds in which they are provided with seed markers.

The at least one marking device can, for example, be adapted for heating or cooling the seeds, in particular to temperatures that differ from the temperature of the soil. The sowing system may in this case further be provided with a temperature measuring device that is capable of determining the temperature of the soil. If seeds are placed in a trench, wherein the seeds have a significant different temperature compared to the soil, then the infrared radiation emitted by the seeds will be different from the infrared radiation emitted by the soil. If the seeds are heated and have a temperature that is higher than the temperature of the soil, the infrared radiation of the seeds will in particular differ from that of the soil so that it can be detected by the at least one detector and at least one filter member of the sensor device. The depth measurement and/or trench profiling may, in this case, be performed by a triangulation arrangement formed by the radiation assembly and another detector of the sensor device. The triangulation can, for example, be performed using either UV-light or visible light provided by the radiation assembly as illumination radiation. This radiation may be detected with at least one further detector. The first detector according to the present invention which blocks the illumination radiation with the filter member can be used to detect the infrared radiation emitted by the seeds because the infrared radiation has a spectral range with wavelengths being longer than those of the illumination radiation.

The sowing system may further comprise seeds provided with at least one marker, the marker having an active or passive radiation emission in the limited spectral range of at least one filter member. The active radiation emission may be induced by fluorescence stimulation by the illumination radiation. The passive radiation emission may be generated by heated or cooled seeds, or other means of luminescence such as chemoluminescence, electroluminescence, photoluminescence, or sonoluminescence.

The present invention and its improvements are described in greater detail below using exemplary embodiments and with reference to the drawings. As described above, the various features shown in the embodiments may be used independently of each other in specific applications.

In the drawings, elements having the same function and/or the same structure will be referenced with the same reference signs.

A sowing system 1 and a sensor device 3 according to the present invention are described with respect to FIG. 1 below. A further description of a sensor device 3 and its various embodiments according to the present invention are also set forth below with respect to FIGS. 2 and 3.

The sowing system 1 can be used for placing seeds 5 into soil 7. The sowing system 1 can be part of or used together with an agricultural device such as a tractor (not shown in the drawings).

The sowing system 1 comprises a cutting device 9 for opening the soil 7 in order to form a trench 11. The trench 11 is only indicated by the dashed line which marks the bottom 13 of the trench 11. The cutting device 9 is adapted for cutting into the ground 15 and, by removing the soil 7, opening the trench 11. The cutting device 9 may, just by way of example, be formed by opener discs for sowing systems.

The sowing device 1 further comprises at least one placement device 17 which is adapted to place seeds 5 in the trench 11. The seeds 5 can be stored in a seed storage volume 19 from which they can be transferred to the placement device 17.

Just by way of example, a marking device 21 is shown between the seed storage volume 19 and the placement device 17. The marking device 21 may, however, also be arranged at another position of the system 1. The marking device 21 may, for example, be part of the seed storage volume 19 or the placement device 17. In the marking device 21, seeds 5 can be provided with at least one seed marker 23, which can, for example, be a fluorescent substance 25. The seed marker 23 in FIG. 1 is applied by spraying onto a seed 5. This is, however, just an example.

The marking device 21 may also be adapted for providing a plurality of seeds 5 with at least one seed marker 23 at the same time. Methods other than spraying can also be used. According to another embodiment of the present invention, the seeds 5 can be marked by heating or cooling the seeds 5 so that their temperature differs from the temperature of the soil 7. In this case, the sowing system 1 may in particular be provided with at least one device (not shown in the drawings) for measuring the temperature of the soil 7.

The sowing system 1 comprises at least one sensor device 3 according to the present invention. The sensor device 3 can, for example, be adapted for measuring the depth 27 of the seeds 5 in the trench 11. Additionally or alternatively, the sensor device 3 may be adapted for measuring the depth 29 of the trench 11. The depth 27 and/or 29 may be measured directly or indirectly. In the case of an indirect measurement, the sensor device 3 measures the distance 31 from the bottom 13 or from the seed 5 in the trench 11 to the device 3. Since the distance 33 between the sensor device 3 and the ground 15 can easily be derived and is therefore regarded as being known, the depth 27 and/or 29 can easily be calculated by subtracting the distance 33 from the distance 31. The sensor device 3 is further adapted for detecting the presence of a seed 5 when the seed 5 is arranged in the region in which the target area (not shown yet) and the field of view (not shown yet) intersect.

It should be noted that the diameter 35 of the seeds 5 can be in the order of millimeters or sometimes tens of millimeters. In this case, the depths 27 and 29 can be regarded as being similar in view of typical aberrations in the measurements. In the case that large seeds 5 are used, for example seeds 5 which have a diameter 35 that is greater than 5 mm, the depth 27 and 29 may be not regarded as being similar. The diameter 35 usually depends on the plant species.

The sensor device 3 comprises a radiation assembly 37 and a detection assembly 39. The radiation assembly 37 generates an illumination radiation 41 towards a target area (not shown yet). The detection assembly 39 has at least one radiation detector 43 for detecting incident radiation 45. The radiation detector 43 has a field of view (not shown yet) that intersects with the target area. If a seed 5 is arranged in the intersection between the target area and the field of view, it can be detected by the sensor device 3. Just by way of example, the radiation detector 43 is shown with a one-dimensional sensor array 47 that allows a triangulation for determining the distance from the sensor device, in particular from the radiation detector 43, to the seed 5. Depending the depth 27 or, respectively 29, a different position of the one-dimensional sensor array 47 is illuminated. The angle of the incident radiation 45 can thereby be determined. The distance 31 can easily be calculated since the radiation assembly 37 and the detection assembly 39 are arranged with a fixed distance to each other.

The one-dimensional sensor array 47 has a longitudinal shape that lies in a plane (not shown) which is formed by a triangle 49 between the radiation assembly 37, the detection assembly 39, and the region in which the target area and the field of view intersect. In FIG. 1, this intersection is where the seed 5 below the sensor device 3 is shown. The triangle 49 is indicated as being formed by the illumination radiation 41, the incident radiation 45, and the dotted line in FIG. 1. The plane of the triangle 49 can, for example, be basically perpendicular to a longitudinal direction 51 of the trench 11. The plane of the triangle 49 can, for example, also basically be perpendicular to the ground 15.

The sensor device 3 as described above forms a triangulation arrangement 53 for determining the position of the seeds 5.

The sowing system 1 can be moved along the longitudinal direction 51 for placing the seeds 5 into the soil 7. The velocity of the movement can easily be measured with appropriate devices. The sowing system 1 can, for example, be moved with a basically constant velocity along the longitudinal direction 51. In order to also determine the spacing of the seeds 5, which is defined by the distance 55 between two adjacent seeds 5, the time between the detections of two adjacent seeds 5 can be measured. The distance 55 between the two adjacent seeds 5 can then easily be calculated as the product of the velocity and the time.

The sowing system 1 comprises at least one closing device 57 for closing the trench 11 subsequent to placing the seeds 5 and determining the seed position with the sensor device 3. The closing device 57 may, for example, comprise two wheels 59 which roll on the ground 15 at the boundary of the trench 11, thereby closing the trench 11 by pressing down the soil 7 so that it fills the trench 11. The closing device 57 may also be used to define the distance 33 from the sensor device 3 to the ground 15.

A first embodiment of a sensor device 3 that can be part of a sowing system 1 according to the present invention is described below with respect to FIG. 2. For the sake of brevity, only the features of the present invention which were not already described above with respect to FIG. 1 are described in detail.

The radiation assembly 37 generates the illumination radiation 41. For this purpose, the sowing system 1 can be provided with at least one radiation source 61. The illumination radiation 41 is oriented towards a target area 63, which is indicated by the circle in FIG. 2. The illumination radiation 41 has an emission spectrum which covers at least a first spectral range. This spectral range can, for example, be in the dark blue or UV-range. In other words, the illumination radiation 41 is matched to the fluorescent substance (seed marker), and thus, for example, has a wavelength lower than 450 nm, for example, lower than 300 nm.

The detection assembly 39, in particular the radiation detector 43 which is adapted for detecting the incident radiation 45, is arranged so that the field of view 65 of the detection assembly 39 intersects with the target area 63. The field of view 65 is indicated by the dotted oval line in FIG. 2.

The detection assembly 39 is provided with a filter member 67 that is arranged in front of the radiation detector 43. The filter member 67 has an attenuation band 68 and a pass band 70, wherein the pass band 70 has less attenuation than the attenuation band 68 in a wavelength range whose wavelengths are longer than those of the attenuation band 68. The bands are indicated in FIG. 2 in the spectrum 72 which depicts the attenuation of the filter member 67 over the wavelength. The filter member 67 may in particular be adapted so that it blocks the illumination radiation 41, but allows radiation having a longer wavelength to pass so that the latter radiation reaches the radiation detector 43. For an improved filter effect, the filter member 67 may be adapted to also block ambient light. The filter thereby selectively allows only the radiation from a fluorescing seed 5 to pass.

Figure 1:
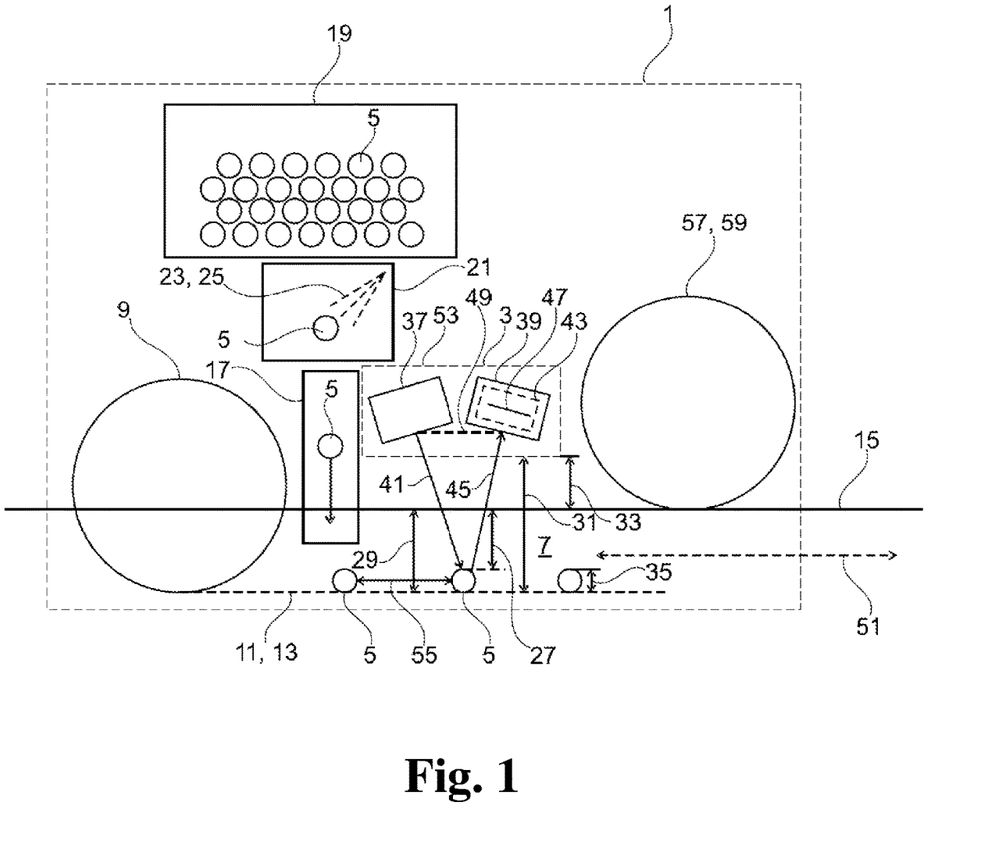
FIG. 1 shows a schematic view of a sowing system according to the present invention.

The radiation detector 43 may be provided with at least one one-dimensional sensor array 47 for performing triangulation measurements as described with respect to FIG. 1.

Figure 2:
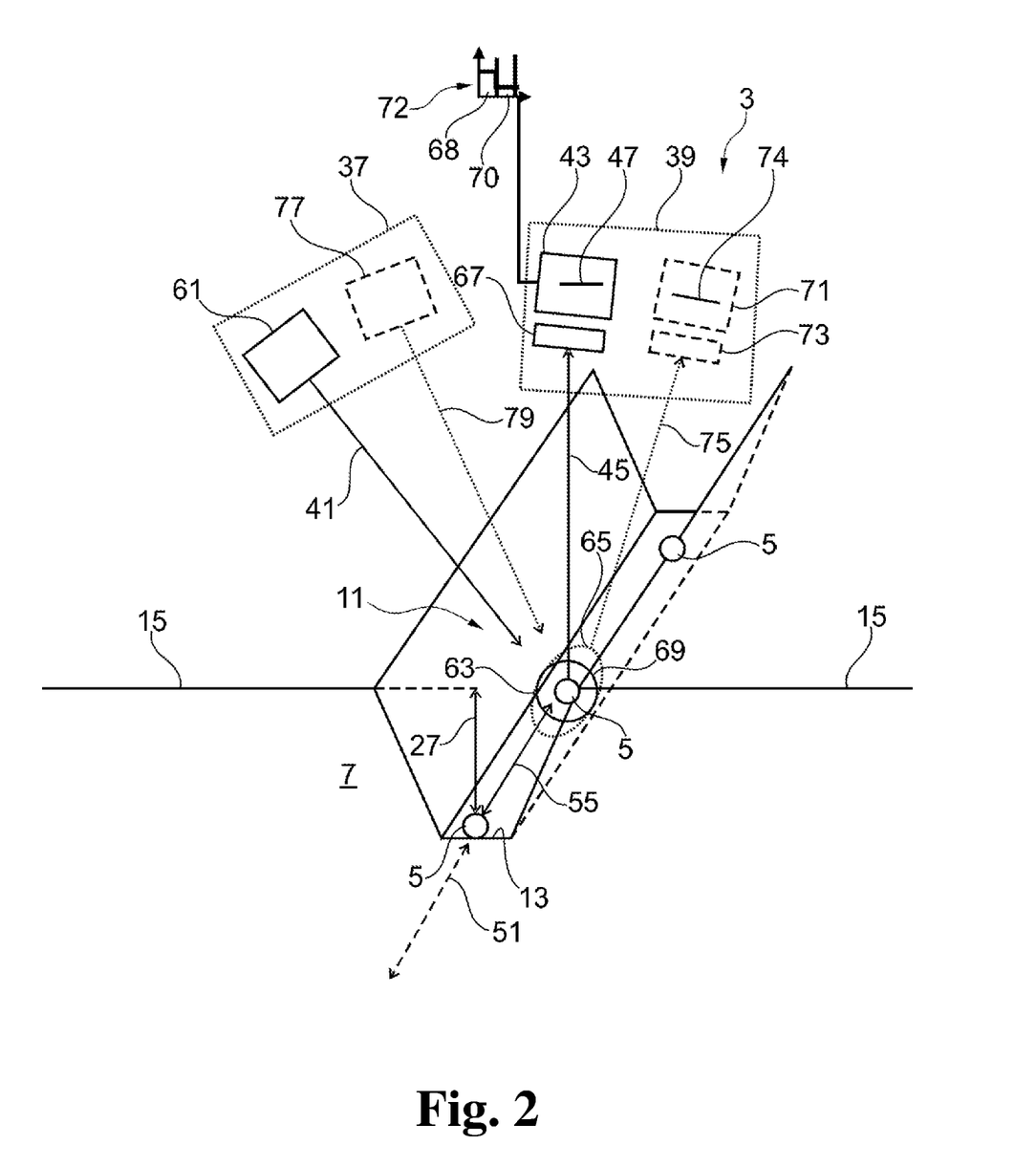
FIG. 2 shows a schematic view of a first embodiment of a sensor device according to the present invention.

The embodiment shown in FIG. 2 is adapted for providing a spot-like area 69 as target area 63. In other words, the radiation source 61 creates an illuminated spot 69. From the illuminated spot 69, radiation may reach the detection assembly 39.

In an embodiment of the present invention, the illumination radiation 41 can, for example, be chosen so that it induces fluorescence emission in the target area 63, in particular from the surface of a seed 5 in the target area 63. The seed 5 may, as described with respect to FIG. 1, be provided with a seed marker 23, such as a fluorescent substance 25. The incident radiation 45 is then formed by the fluorescence radiation that is emitted by the seed 5 and reaches the detection assembly 39. The filter member 67 will allow only this fluorescence radiation 45 to reach the radiation detector 43. The illumination radiation 41 and, for example, other ambient light will be blocked. The presence of a seed 5 can thereby be detected. If the radiation detector 43 is provided with a one-dimensional sensor array 47, the distance 31 (not shown here) can also be measured as described with respect to FIG. 1. The depth 27 of the seeds 5 can thereby be determined. It should be noted that by using this setup and the aforementioned described method, the triangulation may also be performed without a seed 5 in the trench. Fluorescence radiation emitted by the soil 7 that forms the bottom 13 of the trench 11 can thereby be used.

The embodiment as described with respect to FIG. 2 may further be provided with at least one further radiation detector 71 and at least one further filter member 73. The further radiation detector 71 and the further filter member 73 are indicated by the dashed lines. The further radiation detector 71 may be provided with a further one dimensional sensor array 74.

The further radiation detector 71 and the further filter member 73 may be adapted for detecting radiation of the first spectral range. If fluorescence is used, then the further radiation detector 71 and the further filter member 73 may be adapted for detecting the dark blue or UV-radiation provided by the radiation source 61. The incident radiation 75 that passes the further filter member 73 and reaches the further radiation detector 71 consequently differs from the incident radiation 45.

The first radiation detector 43 and the filter member 67 can thereby be used for detecting seeds 5 in the trench 11 via the fluorescence radiation of the seeds 5. The further radiation detector 71 and the further filter member 73 may be used for the triangulation by directly detecting the deep blue or UV incident radiation 75. Each function of the sensor device 3 is thereby performed by a separate detector.

The setup as shown in FIG. 2 may further be improved by providing at least one further radiation source 77 for providing radiation of at least one second spectral range, wherein the wavelengths of the second spectral range are longer than those of the first spectral range. The second spectral range may, for example, be part of visible range. In other words, the further radiation source 77 may provide visible light.

The further radiation source 77 provides illumination radiation 79 that can, for example, illuminate a spot-like target area 63. This setup can, for example, have a radiation source 61 that provides illumination radiation 41 in the deep blue or UV-spectral range and a further radiation source 77 that provides illumination radiation 79 in the visible range. The further radiation detector 71 and the further filter member 73 may here be adapted for detecting the radiation provided by the further radiation source 77. The incident radiation 75 consequently has the same spectral range as the illumination radiation 79, namely, the second spectral range.

The radiation detector 43 and the first filter member 67 can be used, as described further above, for the detection of seeds 5 by detecting fluorescent emissions from the seeds 5. In other words, the detection of the seeds 5 and the depth measurement via triangulation are each performed by a dedicated set of a radiation source, a filter member, and a radiation detector.

At least one of the radiation detectors and its corresponding filter member may be adapted for detecting infrared radiation of the seeds 5 if the seeds 5 are not provided with fluorescent markers, but are thermally treated.

Depending on which radiation detector 43 or 71 performs a triangulation measurement, only this detector 43, 71 may be provided with a one-dimensional sensor array 47 or 74.

A further embodiment of the present invention is described below with respect to FIG. 3. For the sake of brevity, only the differences to the embodiments described with respect to FIG. 2 are described in detail.

Figure 3:
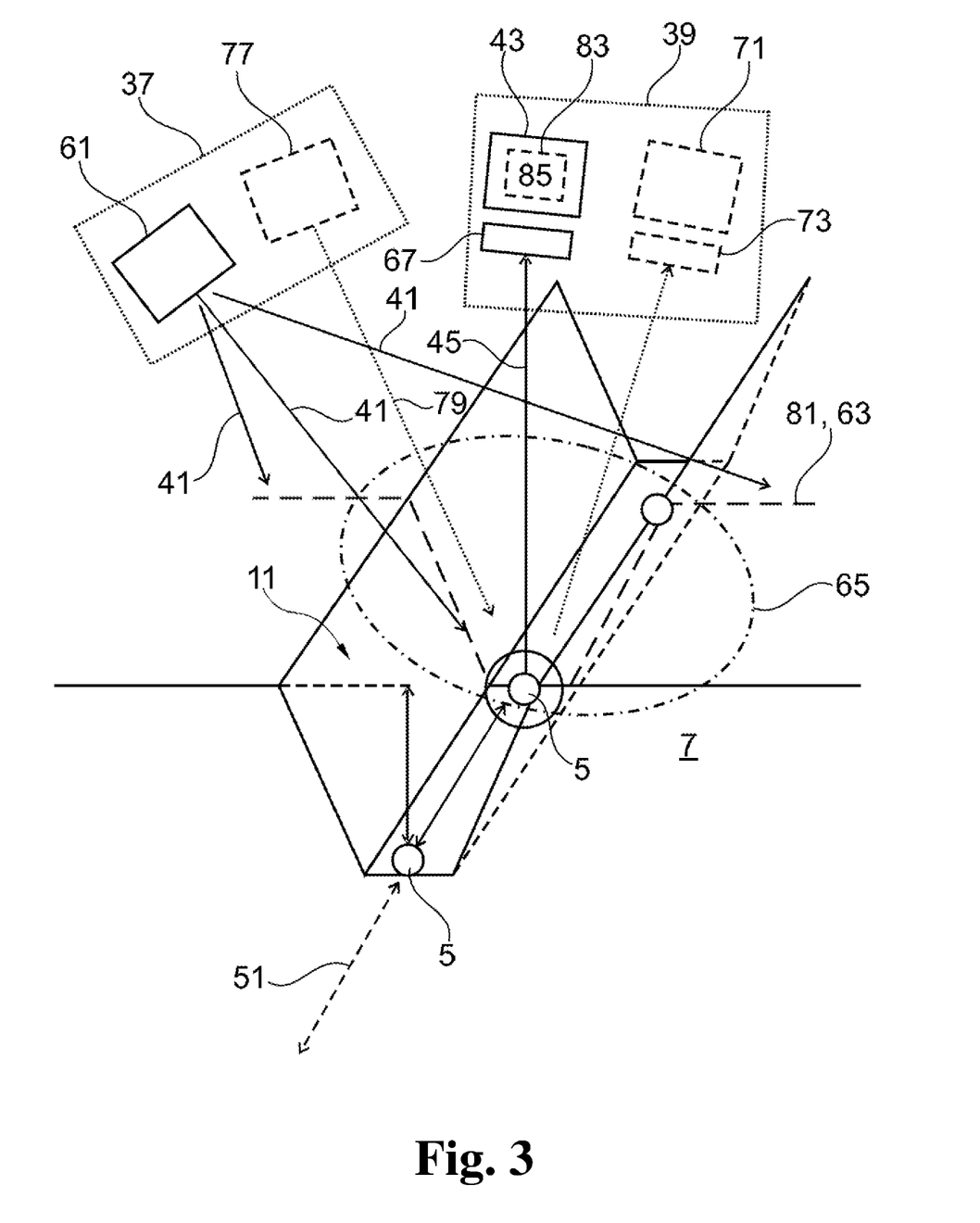
FIG. 3 shows a schematic view of a second embodiment of a sensor device according to the present invention.

The embodiment of FIG. 3 differs from the embodiment as described with respect to FIG. 2 in that at least the radiation source 61 does not irradiate a spot-like area 69, but a line-like area 81. In other words, the radiation source 61 may be a line projector. The line-like area 81 or projected line 81 is indicated by the thick dashed line in FIG. 3.

The radiation detector 43 may be provided with a two-dimensional sensor array 83. The two-dimensional sensor array 83 can, for example, have a sensor plane 85 which is arranged perpendicular to the incident radiation 45. The field of view 65 is adapted for not only detecting a spot-like area around the seed 5, but also at least parts of the line-like illuminated target area 81. Detecting the line-like area 81 with a two-dimensional sensor array 83 makes it possible to determine a trench profile rather than only the depth 29 of the trench. This setup may of course also be used for detecting the presence of a seed 5 in the trench 11.

As with the embodiments described with respect to FIG. 2, the present embodiment may be provided with a further radiation detector 71 and a further filter member 73 that can be used in a similar way as described for the embodiment above. One radiation detector 43 or 71 and its corresponding filter member 67 or 73 may consequently be used for determining the trench profile and the other pair may be used for seed detection. Depending on which radiation detector 43 or 71 is used for which purpose, the further radiation detector 71 could also be provided with a two-dimensional sensor array (not shown). The embodiment may also be provided with at least one further radiation source 77 which can be used to illuminate the seeds 5 or for providing a line-like target area for determining the trench profile (not shown).

The present invention is not limited to embodiments described herein; reference should be had to the appended claims.

What is claimed is:

1. A sensor device for determining a position of seeds while sowing, the sensor device comprising:
   a radiation assembly configured to generate an illumination radiation which is oriented towards at least one target area, the radiation assembly comprising at least one radiation source which is configured to provide a first emission spectrum of the illumination radiation which covers at least a first spectral range; and
   at least one detection assembly comprising,
      at least one radiation detector configured to detect an incident radiation, the at least one radiation detector comprising at least one one-dimensional sensor array and at least one field of view, and
      at least one filter member comprising an attenuation band and a pass band, the pass band comprising an attenuation which is less than an attenuation of the attenuation band in a wavelength range where the wavelengths are longer than those of the attenuation band,
   wherein,
   the at least one target area and the at least one field of view intersect,
   the at least one radiation source is arranged to be spaced apart from the at least one radiation detector,
   the at least one radiation source is configured to irradiate a spot-like area at least in the at least one field of view of the at least one radiation detector, and
   the at least one radiation source of the radiation assembly, the at least one radiation detector, and a region in which the at least one target area and the at least one field of view intersect form a triangulation arrangement which is configured so that a distance from the at least one target area to the at least one detection assembly can be determined.

2. The sensor device as recited in claim 1, wherein the distance is a depth of the seeds.

3. The sensor device as recited in claim 1, wherein,
   the at least one radiation source is configured to irradiate a line-like area at least in the at least one field of view of the at least one radiation detector, and
   the at least one radiation detector further comprises at least one two-dimensional sensor array.

4. The sensor device as recited in claim 3, wherein,
   the distance is a depth of the seeds, and
   the sensor device also determines a trench profile.

5. The sensor device as recited in claim 1, further comprising:
   a seed marker comprising an excitation wavelength,
   wherein,
   the first spectral range comprises wavelengths, and
   the wavelengths of the first spectral range are matched with the excitation wavelength of the seed marker, with each being less than 450 nm.

6. The sensor device as recited in claim 5, wherein
   the at least one detection assembly further comprises at least one further filter member and at least one further radiation detector, and
   the at least one further filter member is configured to let the illumination radiation of the first spectral range pass therethrough.

7. The sensor device as recited in claim 6, wherein,
the radiation assembly further comprises at least one further radiation source which is configured to provide a second emission spectrum of the illumination radiation which covers at least a second spectral range,
the second spectral range comprises wavelengths, and
the wavelengths of the second spectral range are longer than the wavelengths of the first spectral range.

8. A sowing system for delivering seeds into soil, the sowing system comprising:
a cutting device configured to cut a trench;
a placement device configured to place the seeds in the trench;
a closing device configured to close the trench; and
the least one sensor device as recited in claim 6.

9. The sowing system as recited in claim 8, further comprising:
at least one marking device which is configured to mark the seeds with at least one seed marker prior to the seeds being placed in the trench.

10. The sowing system as recited in claim 9, wherein the at least one seed marker is at least one fluorescent substance.

11. The sowing system as recited in claim 9, further comprising:
seeds marked with the at least one seed marker, wherein,
the at least one seed marker comprises an active radiation emission or a passive radiation emission in a limited spectral range of at least one of the at least one filter member and the at least one further filter member.

12. A method for determining a position of seeds in a trench using the sensor device as recited in claim 1, the method comprising:
irradiating at least one target area with an illumination radiation;
detecting an incident radiation received from the at least one target area having longer wavelengths than the illumination radiation with at least one detection assembly;
determining a distance of the at least one target area to the at least one detection assembly in dependence from a position where the incident radiation is received; and
determining a presence of a seed by an optical identification.

13. The method as recited in claim 12, further comprising:
projecting a line with the illumination radiation in the at least one target area; and
determining a trench profile by a space-resolved evaluation of the incident radiation.

14. The method as recited in claim 12, wherein the sensor device as recited in claim 1 further comprises a seed marker which comprises an excitation wavelength, wherein,
the first spectral range of the sensor device comprises wavelengths, and
the wavelengths of the first spectral range are matched with the excitation wavelength of the seed marker, with each being less than 450 nm, and
the method further comprises:
marking the seeds with at least one seed marker.

15. The method as recited in claim 12, wherein the method further uses a sowing system for delivering the seeds into soil, the sowing system comprising:
a cutting device configured to cut a trench;
a placement device configured to place the seeds in the trench; and
a closing device configured to close the trench.

* * * * *